(12) United States Patent
Alper

(10) Patent No.: US 9,102,549 B2
(45) Date of Patent: Aug. 11, 2015

(54) PROCESS FOR PRODUCING COMPOSITIONS FOR USE IN REMOVAL OF DISPERSED, SOLUBILIZED AND/OR EMULSIFIED UNDESIRED SPECIES FROM WATER AND GASES

(75) Inventor: Hal Alper, Flowery Branch, GA (US)

(73) Assignee: MYCELX TECHNOLOGIES CORPORATION, Duluth, GA (US)

( * ) Notice: Subject to any disclaimer, the term of this patent is extended or adjusted under 35 U.S.C. 154(b) by 417 days.

(21) Appl. No.: 13/494,410

(22) Filed: Jun. 12, 2012

(65) Prior Publication Data

US 2012/0316251 A1 Dec. 13, 2012

Related U.S. Application Data

(60) Provisional application No. 61/520,646, filed on Jun. 13, 2011.

(51) Int. Cl.
| | | |
|---|---|---|
| *C09K 3/00* | (2006.01) | |
| *C02F 1/28* | (2006.01) | |
| *A01N 25/34* | (2006.01) | |
| *A01N 61/00* | (2006.01) | |
| *C09D 5/14* | (2006.01) | |
| *C09D 191/00* | (2006.01) | |
| *C08F 242/00* | (2006.01) | |
| *C02F 1/00* | (2006.01) | |

(52) U.S. Cl.
CPC ............... *C02F 1/285* (2013.01); *A01N 25/34* (2013.01); *A01N 61/00* (2013.01); *C08F 242/00* (2013.01); *C09D 5/14* (2013.01); *C09D 191/005* (2013.01); *C02F 1/001* (2013.01); *C08L 2205/02* (2013.01)

(58) Field of Classification Search
None
See application file for complete search history.

(56) References Cited

U.S. PATENT DOCUMENTS

| | | | |
|---|---|---|---|
| 2,160,532 | A | 5/1939 | Barrett et al. |
| 2,418,920 | A | 4/1947 | Berger et al. |
| 2,441,068 | A | 5/1948 | Hewitt et al. |
| 3,067,154 | A | 12/1962 | Sterling |
| 3,755,448 | A | 8/1973 | Merianos et al. |

(Continued)

FOREIGN PATENT DOCUMENTS

| | | |
|---|---|---|
| BE | 859836 | 2/1978 |
| WO | 99/48584 A1 | 9/1999 |

(Continued)

OTHER PUBLICATIONS

D. Swern, ed. Bailey's Industrial Oil and Fat Products vol. 1, Fourth Edition (1979), pp. 687-816.

(Continued)

*Primary Examiner* — Vu A Nguyen
(74) *Attorney, Agent, or Firm* — Sutherland Asbill & Brennan LLP

(57) ABSTRACT

Disclosed is a method of making coagulant and viscoelastic compositions for use in removal of dispersed, solubilized, and emulsified oils and hydrocarbons and other noxious species from water and air. The composition comprises thermal reaction products of blends of fatty acids derived, isolated and purified from drying and semi-drying oils such as linseed, safflower, and tung oil with a polymer such as for example poly(isobutyl methacrylate) and can include a solvent. The product of the invention facilitates cohesion of oils and hydrocarbons independent of agitation and temperature and may be used in both salt and fresh water, air and other gaseous streams.

10 Claims, 8 Drawing Sheets

(56) References Cited

U.S. PATENT DOCUMENTS

| | | |
|---|---|---|
| 3,776,864 A | 12/1973 | Woerner |
| 3,821,109 A | 6/1974 | Gilchrist et al. |
| 3,835,049 A | 9/1974 | King |
| 3,917,528 A | 11/1975 | Orban et al. |
| 3,977,969 A | 8/1976 | Zall |
| 4,156,040 A | 5/1979 | Swider et al. |
| 4,200,561 A | 4/1980 | Chang |
| 4,313,830 A | 2/1982 | Tulin et al. |
| 4,316,730 A | 2/1982 | Eibl |
| 4,420,400 A | 12/1983 | Weitzen |
| 4,420,573 A | 12/1983 | Fogg et al. |
| 4,502,975 A | 3/1985 | Kobayashi et al. |
| 4,519,918 A | 5/1985 | Ericsson et al. |
| 4,786,717 A | 11/1988 | Bretches et al. |
| 4,810,395 A | 3/1989 | Levy et al. |
| 4,964,987 A | 10/1990 | Johnson |
| 5,122,270 A | 6/1992 | Ruger et al. |
| 5,213,689 A | 5/1993 | Kafchinski et al. |
| 5,259,952 A | 11/1993 | Lee |
| 5,326,394 A | 7/1994 | Cobb |
| 5,382,371 A | 1/1995 | Stahl et al. |
| 5,405,932 A | 4/1995 | Bender et al. |
| 5,427,612 A | 6/1995 | Bender |
| 5,429,741 A | 7/1995 | Webb et al. |
| 5,437,793 A | 8/1995 | Alper |
| 5,527,466 A | 6/1996 | Li et al. |
| 5,698,139 A | 12/1997 | Alper |
| 5,746,925 A | 5/1998 | Alper |
| 5,837,146 A | 11/1998 | Alper |
| 5,919,944 A | 7/1999 | Eldin |
| 5,961,823 A | 10/1999 | Alper |
| 6,001,244 A | 12/1999 | Salter et al. |
| 6,168,714 B1 | 1/2001 | Ilias et al. |
| 6,180,010 B1 | 1/2001 | Alper |
| 6,337,016 B1 | 1/2002 | Alper |
| 6,475,393 B2 | 11/2002 | Alper |
| 6,491,822 B2 | 12/2002 | Alper |
| 6,623,513 B2 | 9/2003 | Biel |
| 6,805,727 B2 | 10/2004 | Alper |
| 6,883,321 B2 | 4/2005 | Fornof |
| 7,264,721 B2 | 9/2007 | Alper |
| 7,264,722 B2 | 9/2007 | Alper |
| 7,449,119 B2 | 11/2008 | Brown |
| 8,187,459 B2 | 5/2012 | Alper |
| 2001/0042720 A1 | 11/2001 | Alper |
| 2007/0023357 A1 | 2/2007 | Brown |
| 2010/0249267 A1 | 9/2010 | Jiang et al. |

FOREIGN PATENT DOCUMENTS

| | | |
|---|---|---|
| WO | 2009/061462 A1 | 5/2009 |
| WO | 2010/089598 A1 | 8/2010 |

OTHER PUBLICATIONS

D. Swern, ed. Bailey's Industrial Oil and Fat Products vol. 1, Fourth Edition (1979), pp. 687-747.
International Search Report and Written Opinion for PCT/US2012/042030 mailed Sep. 11, 2012.
International Search Report and Written Opinion for PCT/US2012/042031 mailed Sep. 20, 2012.

PROCESS FOR PRODUCING COMPOSITIONS FOR USE IN REMOVAL OF DISPERSED, SOLUBILIZED AND/OR EMULSIFIED UNDESIRED SPECIES FROM WATER AND GASES

CROSS-REFERENCE TO RELATED APPLICATIONS

This application claims priority from U.S. provisional patent application Ser. No. 61/520,646, filed on Jun. 13, 2011, which is incorporated herein by reference in its entirety.

FIELD OF INVENTION

This invention relates to a composition and method for producing same, the composition being for use in removal of dispersed, solubilized, and/or emulsified oils, hydrocarbons, microbes, endotoxins, triglycerides, and cholesterol from water and benign gases.

BACKGROUND OF INVENTION

Oils and hydrocarbons as a class lack a singular, direct stoichiometric functionality, which renders them not amenable to separation processes based on specific reactive functionalities. Therefore, separation methods for these compositions dating back millennia have relied on broad general properties, such as their relative buoyancy in relation to water, resulting in a variety of gravity based separation technologies, including those based on centrifuges, underflow weirs, parallel and inclined plate separators, and on porous and non-porous materials the surfaces of which are employed to force smaller droplets into more buoyant larger droplets. The other primary method for separation for this group of compositions has been the use of adsorptive surfaces, which rely on the mutual attraction of these compositions for said surfaces, driven by weak molecular interactions such as Van der Waals forces. The present invention exploits a common trait of this broad category of compositions, namely, their tendency to self-assemble based on cohesion to each other due to the organizing tendency of hybridized pi-orbitals.

In the present inventor's U.S. Pat. No. 6,180,010, it is disclosed that the compositions described in the inventor's U.S. Pat. Nos. 5,437,793; 5,698,139; 5,837,146; and 5,961,823, (all of which disclosures are hereby incorporated by reference in their entireties) have extremely strong affinities for the aforementioned contaminants in water; and that such compositions can not only be used to directly agglomerate oil spills and the like in bodies of water, but further, that when aqueous streams containing these noxious contaminants are passed through filtration media incorporating these compositions, the contaminants are immobilized at the media, as a result of which concentration levels of the contaminants in the filtrate may be reduced to very low values. Still further, in the inventor's U.S. Pat. No. 6,805,727 (the disclosure of which is hereby incorporated by reference in its entirety), it was found that the said compositions may be used in infused filtration media to remove noxious hydrocarbons and oils, as well as other finely suspended liquid and solid particulates and aerosols, which are dispersed in air or other benign gases. The said prior art absorption composition (referred to herein for convenience as the "PAAC") generally comprised a homogeneous thermal reaction product of an first reactant selected from the group consisting of glycerides, fatty acids, alkenes and alkynes, and a methacrylate or acrylate polymer component. Most commonly, the first reactant in the previous invention was a commercially available drying oil (comprised of poly-unsaturated glyceride esters of fatty acids containing one or more double bonds, in which at least two of the fatty acids contain conjugated double bonds). These glycerides, such as linseed oil or tung oil, may be derived from animal or vegetable sources. The polymer component can be derived from alpha and beta unsaturated carbonyl compounds.

SUMMARY OF INVENTION

Now in accordance with the present invention, a method has been found for producing a new and unexpectedly improved composition for use in removal of dispersed, solubilized, and emulsified oils, hydrocarbons, microbes, endotoxins, triglycerides, and cholesterol, from water, and from air and other benign gases. The thermal reaction producing the PAACs, as is indicated above, have in most cases employed as the first reactant the aforementioned fatty acid esters, i.e. by direct use of a drying oil such as linseed oil, or tung oil. Also it has been mentioned in my prior patents that the reactant could be a fatty acid. In the present invention a completely different first reactant is used, with surprisingly unexpected results in performance of the resulting product, and indeed in the product per se.

Thus in accordance with the present invention, an initial glyceride composition is provided which comprises one or more drying oils and/or semi-drying oils. This composition/compound is not, however, used as in the prior art, i.e. as the first reactant to produce a PAAC. Rather it is subjected to a cleaving and separating step to yield a blend comprised of purified saturated and mono and poly unsaturated fatty acids, the fatty acid blend being unique to the initial glyceride composition. It is this unique fatty acid blend which is then thermally reacted with a methacrylate or acrylate polymer compound to yield a homogeneous thermal reaction product having coagulation and viscoelastic rheology modification properties.

The thermal reaction product is found to itself be a uniquely distinct composition, which possesses considerably enhanced characteristics and effectiveness when employed in uses including those with which the PAACs have heretofore been used.

The compositions of the invention are not only useful in separation of oil and hydrocarbons as such, but moreover are found useful in separation from water and gases of further noxious contaminants, including microbes, endotoxins, triglycerides, and cholesterol. While the exact mechanism acting to remove these further species is not totally understood, a hypothesis has been developed regarding the nature of the mechanism.

While not intending to be bound by theory, the hypothesis observes that exterior portions of most cells, including algae, plankton, sulfate reducing bacteria and protists, are composed of a cell membrane, the major constituent of which is a lipid bi-layer, encased in the exoplasmic surface of the cell composed of exopolysaccharide/glycolipid assemblages. The lipid bi-layer is composed of phospholipids which are the diglyceride esters of mono-unsaturated or polyunsaturated fatty acids of glycerin phosphate. This layer almost always contains the essential fatty acids (alpha-linolenic acid and linoleic acid) and usually includes gamma-linolenic acid, and palmitoleic acid (monounsaturated). These same fatty acids can be derived/obtained from drying oils and semi-drying oils in the starting form of triglyceride esters from fish (menhaden oil), flaxseed (linseed oil), hemp oil, soy oil, rapeseed, sunflower seed and a great many other oily seeds and from olives. The exoplasmic surface of the cell is a complex agglomeration of exopolysaccharides ("EPS"). These vary greatly in composition, but they are usually polyanionic due to the presence of uronic acids or ketal linked pyruvate. These polysaccharides yield highly viscous aqueous solutions with viscoelastic properties. Glycolipids are obtained when a carbohydrate chain is bonded to a phospholipid on the exoplasmic surface of the cell. They can exist in the form of glycolipid (sugar bonded directly to the fatty acid) or glycerolglycolipid (sugar bonded to glycerin of diglyceride fatty acid ester). Glycolipids also always contain essential and other polyunsaturated, mono-unsaturated and saturated fatty acids some of which are identical and others similar to those derived from seed oils yielding drying, semidrying and nondrying oils. The formation of a tertiary structure due to the interaction of the lipids and polysaccharides is known as biofilm formation. This biofilm can occur on the cell and on other surfaces as a result of interactions of living cells or resulting from the decomposition of dead cells. The resultant film is usually viscoelastic and amphiphatic in its water solubility characteristics.

This biofilm is the medium/matrix upon which newly produced cells anchor themselves to a substrate and to each other. Production and propagation of this film through a substrate or filter media in conjunction with cellular reproduction results in the primary mechanism by which cells and microbial matter are able to penetrate, saturate and be discharged through filter media (e.g. non-wovens such as MBPP (melt blown polypropylene)), and granular material such as clay, sand and granular activated carbon) which is initially able to intercept and prevent mechanical penetration and breakthrough of the microbes. This phenomenon, known as grow-through results in penetration and discharge/breakthrough of microbes through filter media which may be sufficiently fine or efficient enough to initially intercept and prevent discharge of microbes and microbial matter through purely physical/mechanical breakthrough. It is theorized that microbes captured by filters infused with the compositions of the invention are unable to anchor on the substrate or to adhere to each other and multiply due to incorporation or denaturing of the EPS (exopolysaccharide) matrix. This denaturing is probably the result of the high affinity of the EPS for the compositions due to their very similar physiochemical properties.

The thermal reaction product(s) of the invention (herein "TRPI") is the product (thermally driven self-assembling phase transition product) of fatty acid blends cleaved from triglyceride esters of drying and/or semi drying oils (the same fatty acids as contained in glycosaccharides and phospholipids) and IBMA (isobutyl methacrylate) and n-BMA (n-butyl methacrylate) (similar in properties to EPS). The result is a polymer which can be used as is or can be cured on to surfaces and in which other viscoelastic, film forming (water insoluble or semi-soluble solvents) or coacervate forming (oils) materials are very soluble. Contact of the TRPI with these materials results in a cohesive viscoelastic water insoluble mass. Therefore filters and other surfaces infused with TRPI have the ability to incorporate and remove from solution oils, EPS, solvents, fatty acids, cholesterol microbes and microbial decomposition products (especially endotoxins and film formers) with very little resistance to flow due to the viscoelasticity of the resultant cohesive mass. PAACs have also shown the ability to capture endotoxins from a liquid carrier (U.S. Pat. No. 7,449,119). Furthermore, PAACs have been found able to capture living cells and endotoxins from gaseous carriers without themselves becoming septic (PCT/US2008/012558 and U.S. Pat. No. 6,805,727), and this finding also pertains to TRPI. It is theorized that cells captured on a PAAC— or TRPI-infused surface are unable to multiply due to incorporation of the exopolysaccharide biofilm matrix which the multiplying cell must exude in order for the new cell to anchor itself and to protect the new cell from the environment.

BRIEF DESCRIPTION OF DRAWINGS

In the drawings appended hereto.

DESCRIPTION OF PREFERRED EMBODIMENT

Figure 1:
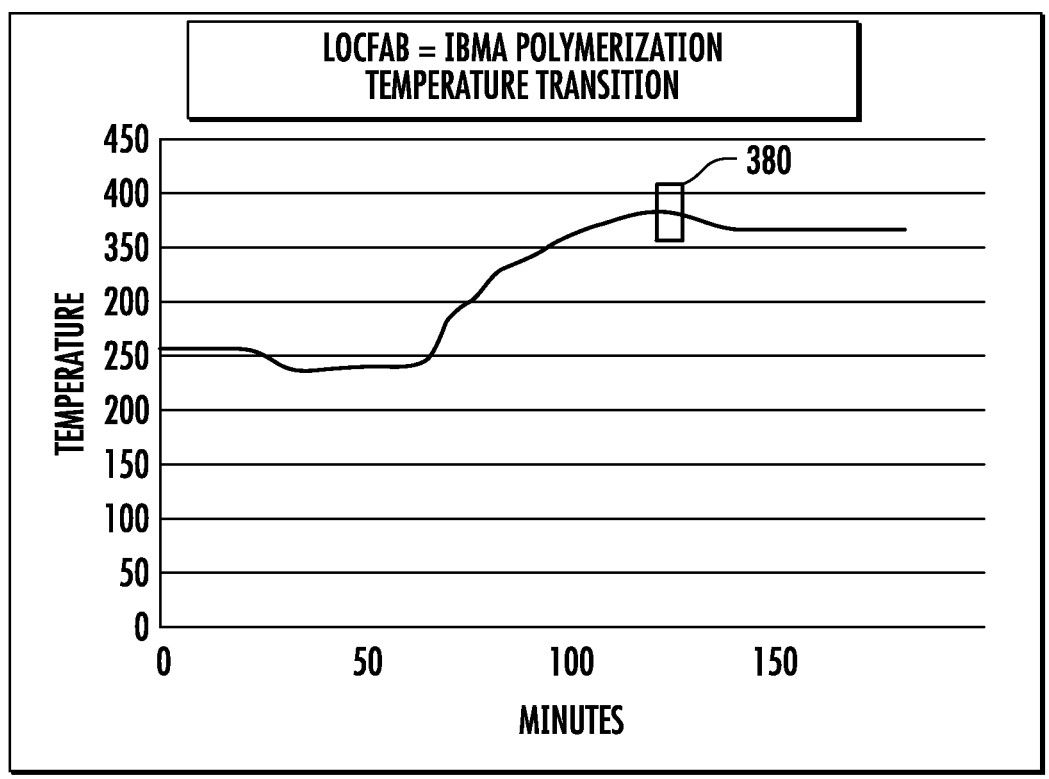
FIG. 1 is a plot of temperature vs. time during synthesis of the thermal reaction product of a linseed oil constituent fatty acid blend (LOCFAB) with an isobutyl methacrylate polymer (IBMA) in accordance with the present invention.
Figure 2:
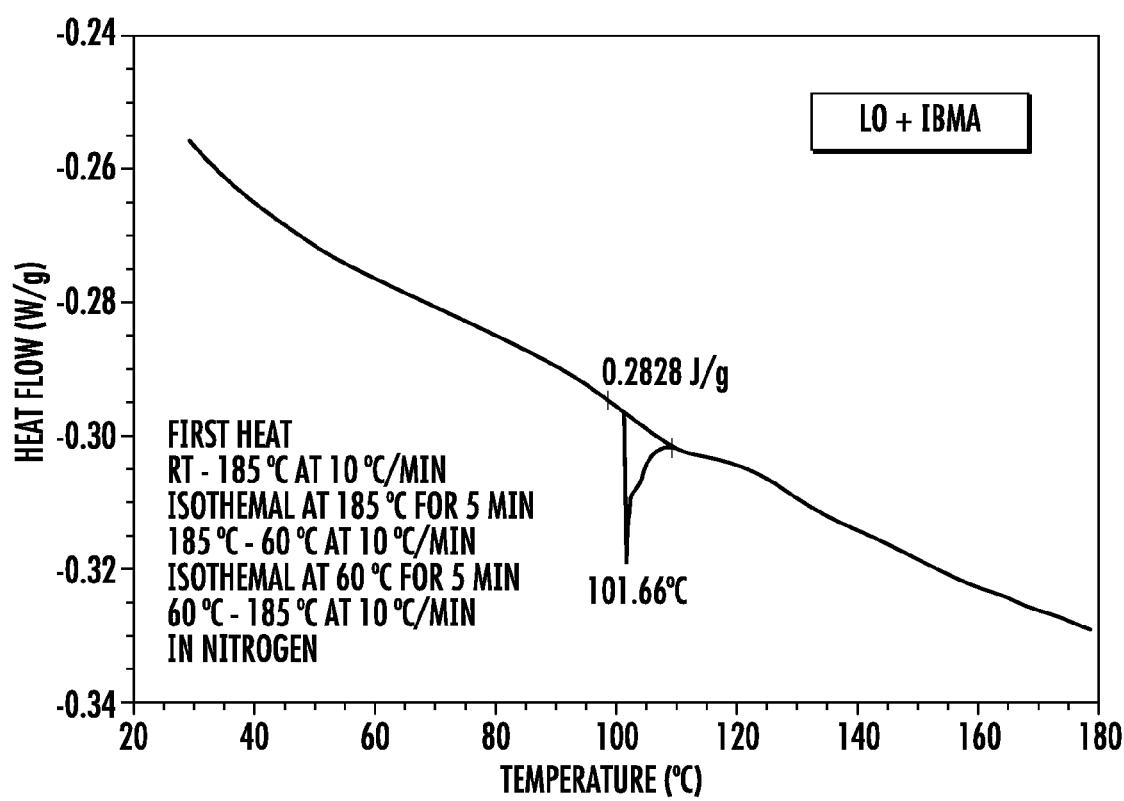
FIG. 2 is a plot yielded where Differential Scanning calorimetry (DSC) was performed on the reaction products from the thermal reaction of linseed oil (LO) with an isobutyl methacrylate polymer (IBMA)
Figure 3:
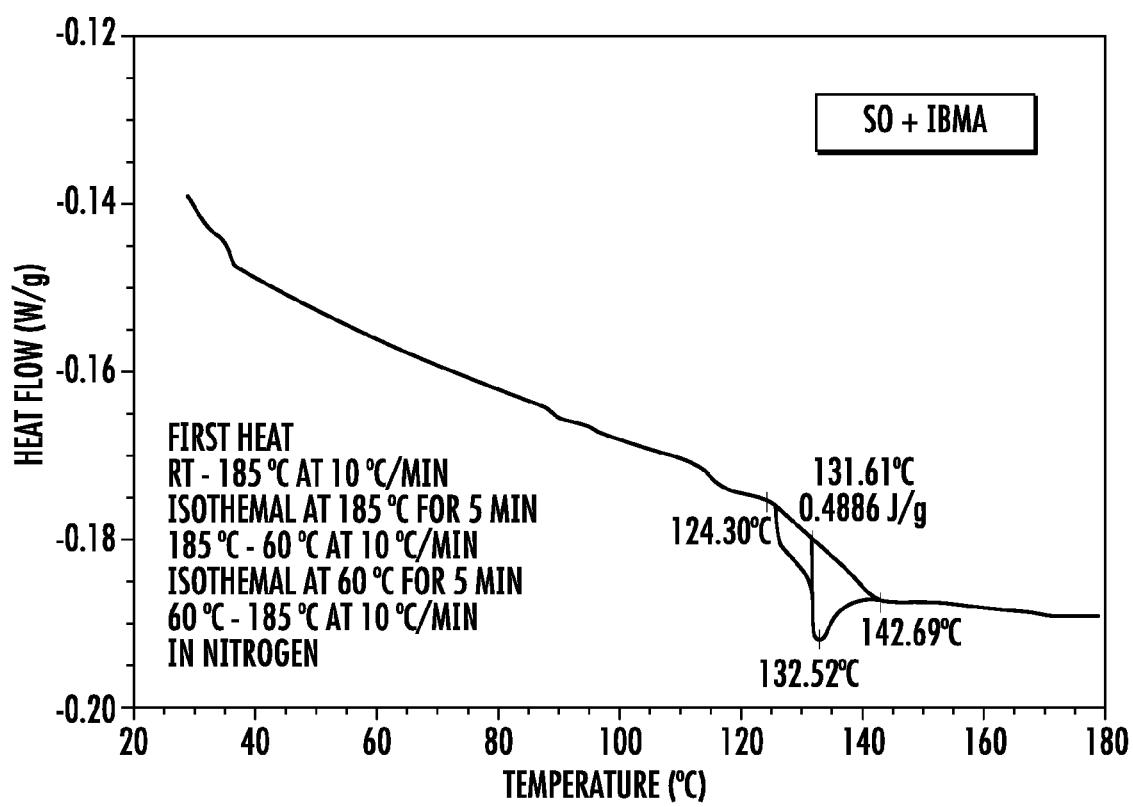
FIG. 3 is a plot yielded where Differential Scanning calorimetry was performed on the reaction products from the thermal reaction of safflower (SO) with an isobutyl methacrylate polymer (IBMA)
Figure 4:
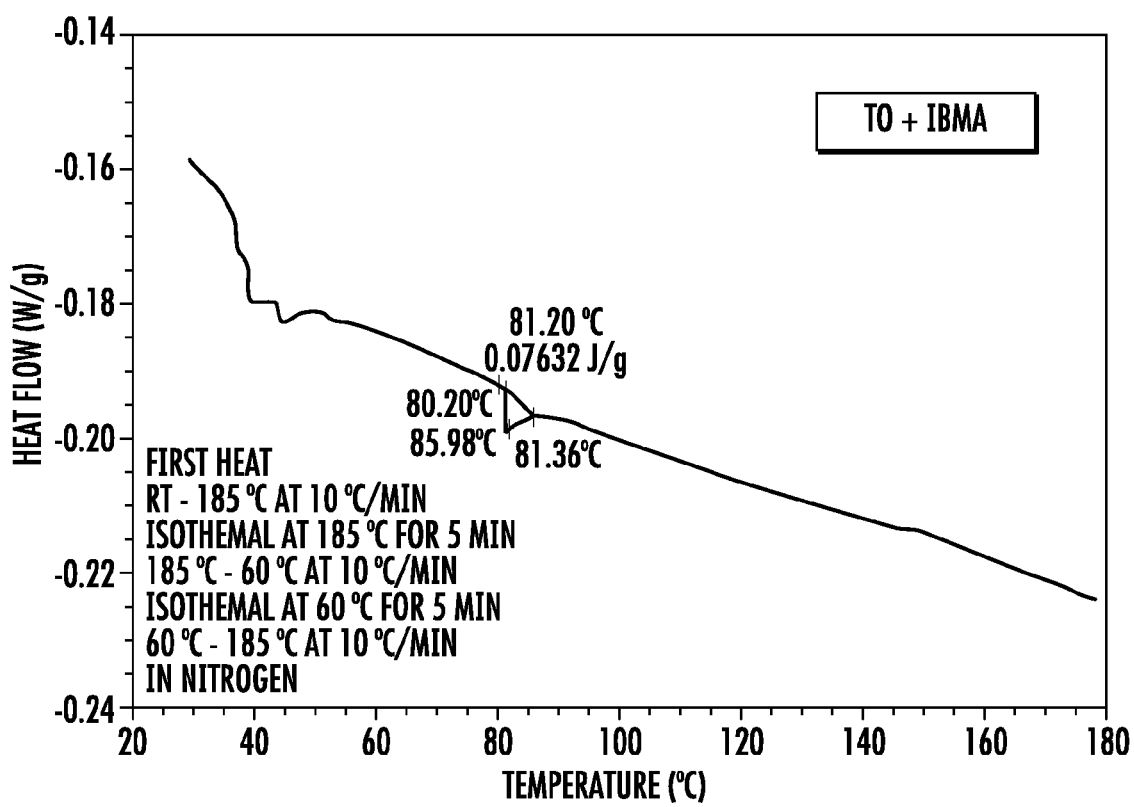
FIG. 4 is a plot yielded where Differential Scanning calorimetry was performed on the reaction products from the thermal reaction of tung oil (TO) with an isobutyl methacrylate polymer (IBMA)
Figure 5:
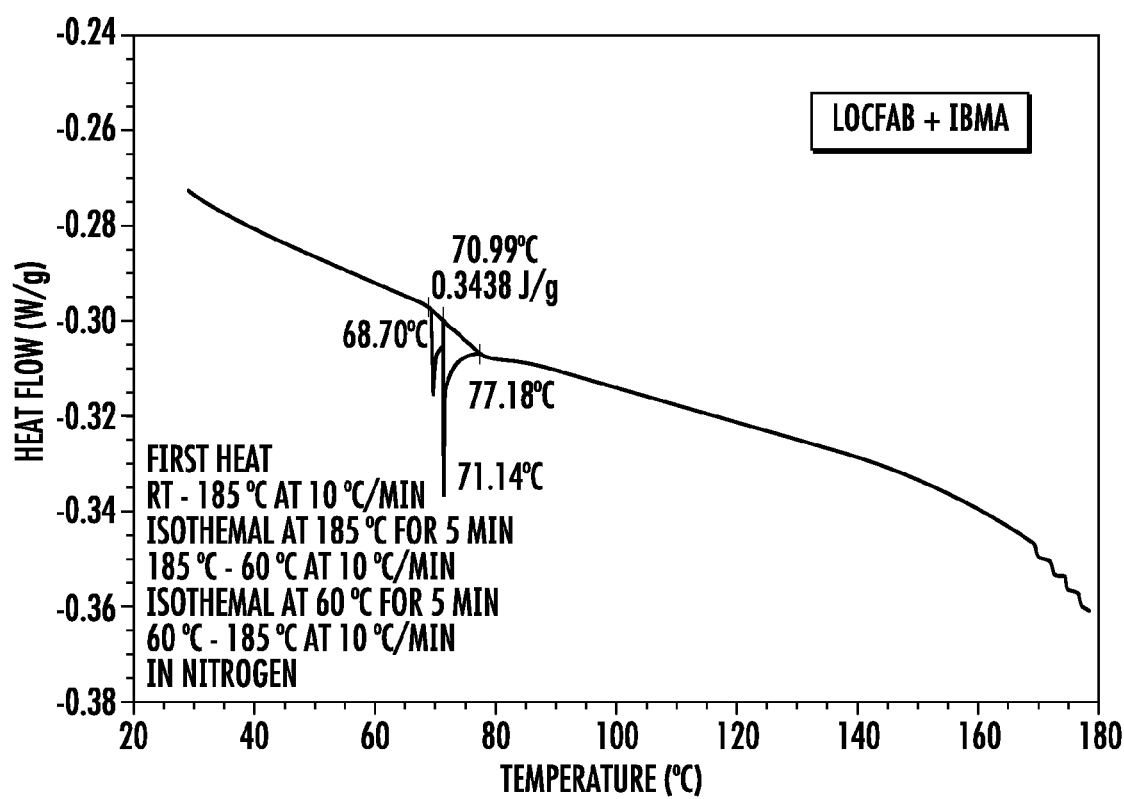
FIG. 5 is a plot yielded where Differential Scanning calorimetry was performed on the reaction products from the thermal reaction of linseed oil constituent fatty acid blend (LOCFAB) with an isobutyl methacrylate polymer (IBMA)
Figure 6:
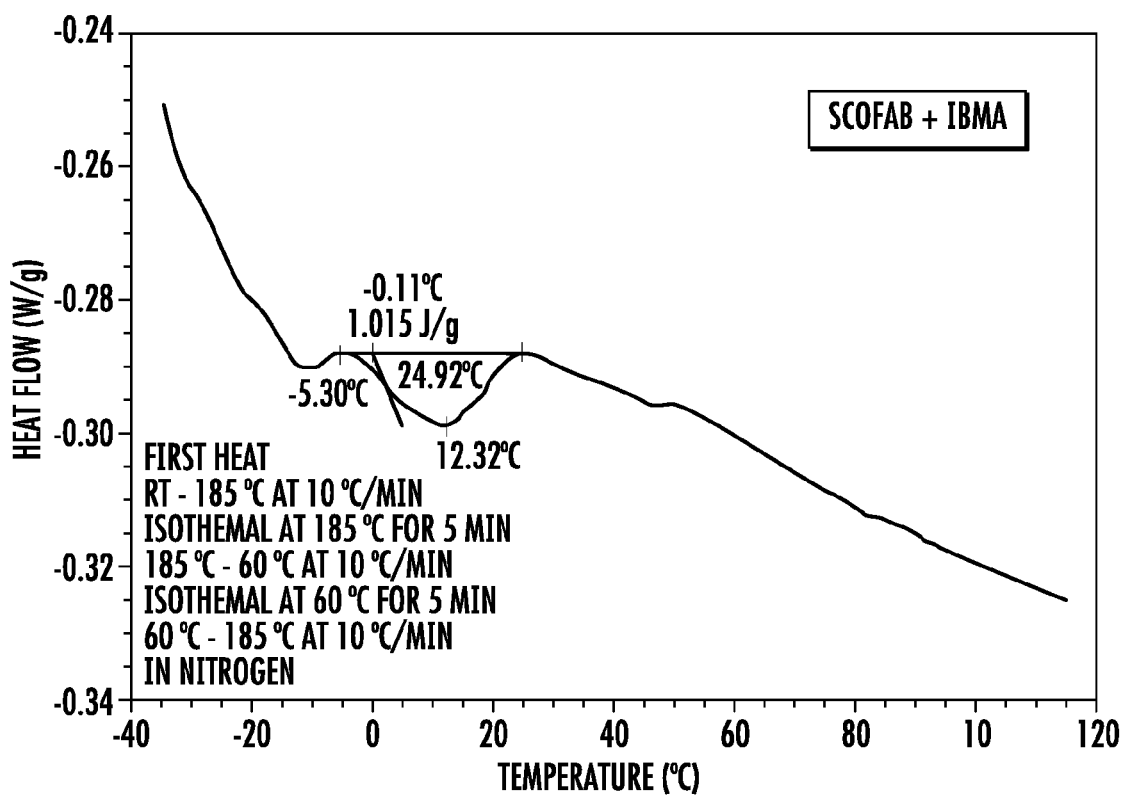
FIG. 6 is a plot yielded where Differential Scanning calorimetry was performed on the reaction products from the thermal reaction of safflower oil constituent fatty acid blend (SOCFAB) with an isobutyl methacrylate polymer (IBMA)
Figure 7:
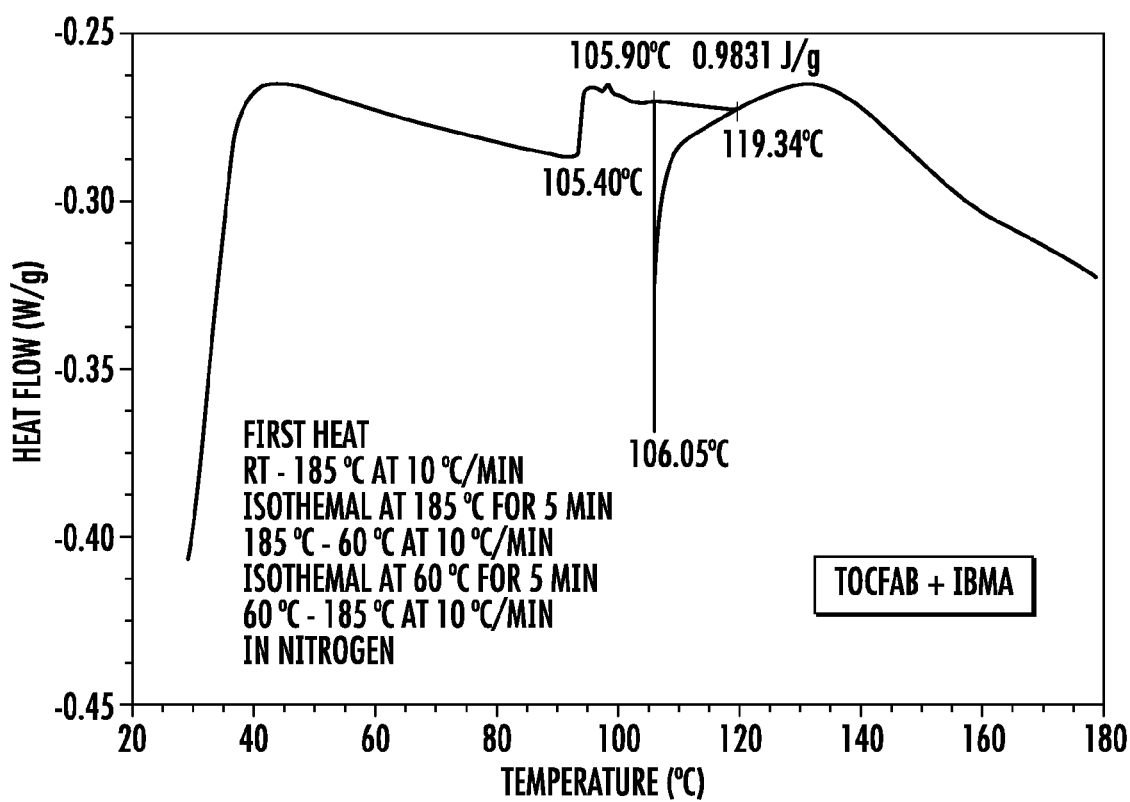
FIG. 7 is a plot yielded where Differential Scanning calorimetry was performed on the reaction products from the thermal reaction of tung oil constituent fatty acid blend (TOCFAB) with an isobutyl methacrylate polymer (IBMA)

The present invention thus involves the cleavage and separation of the fatty acids from the initial drying oil/semi-drying oil composition, yielding a unique blend of saturated and mono and poly unsaturated fatty acids which are then caused to undergo a thermal reaction with the aforementioned polymer component, yielding a novel complex self-assembled reaction product (a TRPI) which is viscoelastic and has the ability to exploit and enhance the cohesive tendency of oils, hydrocarbons, and other noxious species, based on complex pi-orbital interactions to yield a cohesive viscoelastic mass. The TRPI can therefore be used in direct coagulation applications, or can be impregnated and cured into a variety of organic and inorganic substrates, which can then serve in filtration uses.

In the first step of the present process, an initial glyceride composition is provided which comprises one or more drying oils and/or semi-drying oils. The drying oils used are preferably those having an Iodine Number greater than 130, and the semi-drying oils as having an Iodine Number in the range of 115 to 130. In many uses for which PAACs were used, the thermal reaction products of the present invention (TRPI) will be prepared from an initial glyceride composition comprising only one or more drying oils, i.e. such as linseed oil, safflower oil, tung oil, soybean oil, menhaden oil, hemp oil, and mixtures thereof. However in these and further uses, one or more semi-drying oils may also be incorporated in the initial step of the process, as these semi-drying oils can lend some increased softness or flexibility to the final viscoelastic TRPI.

This initial glyceride composition is subjected to a cleaving and separating step to yield a blend comprised of purified saturated and mono and poly unsaturated fatty acids, the fatty acid blend being unique to the initial glyceride composition. Cleaving of the fatty acids can be effected by saponification of the initial glyceride oil composition, followed by acid neutralization of the resulting soap to free the fatty acids therein. Alternatively, the cleaving of the fatty acids can be effected by hydrolyzing the ester bonds of the corresponding glycerides, freeing the fatty acids together with glycerin, followed by separation of the fatty acid to then comprise the fatty acid blend for the subsequent thermal reaction. The fatty acid blend prepared in this manner is referred to herein as the constituent fatty acid blend ("CFAB").

The, isolated and purified blend of fatty acids derived from the foregoing steps is then thermally reacted with a polymer such as for example poly(isobutyl methacrylate) and can include or not include a solvent such as for example 2,2,4-trimethyl-1,3-pentanediol-monoisobutyrate, d-limonene, or aromatic hydrocarbons such as benzene. The thermal reaction product of the invention facilitates cohesion of oils, hydrocarbons, and other noxious species independent of agitation and temperature, and may be used in both salt and fresh water, as well as in purification of air and other gaseous streams. After contact with the cohesive agent product, the oils and hydrocarbons yield a single cohesive viscoelastic mass. The thermal reaction product can be used by introduction of the liquid phase into the stream or via infusion and curing into a substrate through which the liquid or a gaseous stream is passed.

The reaction product can e.g. be delivered alone or dissolved into a carrier vehicle, directly to an aqueous waste stream resulting in dissolution of the dispersed or solubilized hydrocarbons into the reaction product yielding a buoyant viscoelastic mass which is then easily separated through mechanical means. The reaction product can also be delivered through infusion and curing into or onto a porous or non-porous substrate material, such as a filter which can be composed of porous and non-porous silica, paper, and synthetic polymers such as melt blown polypropylene (MBPP), a porous ceramic, a porous metal, a mineral particulate such as vermiculite or perlite, or so forth. (Filtration media of this type are disclosed in detail in the present applicant's U.S. Pat. No. 6,190,010, the disclosure of which is incorporated herein by reference in its entirety). The waste stream is passed through the infused filter causing the constituent organic hydrocarbon and oily pollutants to cohere to each other and to the substrate as a viscoelastic mass. The viscoelasticity of the resultant mass allows for the coagulation for a large amount of hydrocarbons while developing a minimal amount of differential pressure (generally less than 1 psi until filter saturation). The polymerically modified substrate can also be used by allowing it to saturate with the hydrocarbons or other species to be removed, and allowing the hydrocarbons to break through transforming the dispersed hydrocarbons into a cohesive hydrophobic buoyant single mass which is then easily mechanically separated from the water.

The present invention is further illustrated by the following Examples, which are indeed to be considered as merely exemplary and not delimitative of the invention otherwise described.

EXAMPLES

Example 1

Cleavage Reactions (a) Isolation of Fatty Acids from Linseed Oil.

200 g of linseed oil and 38.27 g of potassium hydroxide was charged in a beaker with magnetic stirrer, heated and stirred continuously at 80-85° C. for about one hour. After the saponification was complete (thickening and formation of visible glycerin layer), the mixture was cooled in water bath and filtered to separate the soap from the glycol. The pH of the soap was around 10. The soap was acidified with concentrated hydrochloric acid to pH 4. Acidification of the soap springs free fatty acid with potassium chloride by product. The fatty acids were separated from the salt by decanting. Samples of the blend of fatty acids were then subjected to GS/MS (gas chromatography/mass spectrometry) and FAME (fatty acid methyl ester) analysis.

An off-the-shelf ("OTS") commercial linseed oil was subjected to analysis to provide comparison data. The result is shown in Table A below:

TABLE A

Content of methyl esters in OTS linseed oil expressed as fatty acids

| Component | % of Total |
| --- | --- |
| Palmitic | 22.40 |
| Linoleic | 7.35 |
| Oleic | 53.33 |
| Stearic | 16.92 |
| Total | 100.00% |

The analysis of the fatty acid blend resulting from the cleaving of the OTS linseed oil, yielded the results shown in Table B below.

TABLE B

Content of fatty acids in linseed oil constituent fatty acid blend ("LOCFAB")

| Component | % of Total |
| --- | --- |
| Palmitic | 16.11 |
| Linoleic | 8.33 |
| Oleic | 65.53 |
| Stearic | 12.03 |
| Total | 100.00% |

The marked difference in the fraction of the same fatty acids respectively in Tables A and B indicates that the cleavage and separation has yielded an unexpected result.

(b) Isolation of Fatty Acids from Safflower Oil.

200 g of safflower oil and 38.27 g of potassium hydroxide was charged in a beaker with magnetic stirrer, heated and stirred continuously at 80-85° C. for about one hour. After the saponification was over, the mixture was cooled in water bath and filtered to separate the soap from the glycol. The pH of the soap was around 10. The soap was acidified with concentrated hydrogen chloride to pH 4. Acidification of the soap springs free fatty acid with potassium chloride by product. The fatty acid was separated from the salt by decanting, and the samples were then subjected to GC/MS (gas chromatography/mass spectrometry) and FAME (fatty acid methyl ester analysis).

An off-the-shelf ("OTS") commercial safflower oil was subjected to analysis to provide further comparison data. The result is shown in Table C below.

TABLE C

Content of methyl esters in OTS safflower
oil expressed as fatty acids

| Component | % of Total |
|---|---|
| Palmitic | 10.18 |
| Linoleic | 2.11 |
| Oleic | 82.73 |
| Stearic | 5.34 |
| Total | 100.00% |

The analysis of the fatty acid blend resulting from the cleaving of safflower oil, yielded the results shown in Table D below.

TABLE D

Content of fatty acids in safflower oil constituent
fatty acid blend ("SOCFAB")

| Component | % of Total |
|---|---|
| Palmitic | 12.77 |
| Linoleic | 51.70 |
| Oleic | 30.45 |
| Stearic | 5.08 |
| Total | 100.00% |

Note the extreme differences from Table C to Table D in the fractions of identical fatty acids, which are unexpected and which apparently result from the process steps of the invention.

(c) Isolation of Fatty Acids from Tung Oil.

200 g of an OTS commercial tung oil and 38.27 g of potassium hydroxide was charged in a beaker with magnetic stirrer, heated and stirred continuously at 80-85° C. for about one hour. After the saponification was over, the mixture was cooled in water bath and filtered to separate the soap from the glycol. The pH of the soap was around 10. The soap was acidified with concentrated hydrogen chloride to pH 4. Acidification of the soap springs free the fatty acids with potassium chloride as a byproduct. The fatty acids were separated from the salt by decanting, and the samples were then subjected to GC/MS (gas chromatography/mass spectrometry) and FAME (fatty acid methyl ester) analysis.

The off-the-shelf ("OTS") commercial tung oil was also subjected to analysis to provide comparison data. The result is shown in Table E below.

TABLE E

Content of methyl esters in OTS tung oil expressed as fatty acids

| Component | % of Total |
|---|---|
| Palmitic acid | 2.46% |
| Linoleic acid | 6.10 |
| Oleic acid | 8.87 |
| Stearic acid | 3.07 |
| α-linoleic acid | 79.50 |
| Total (including trace components) | 100.00% |

The analysis of the fatty acid blend resulting from the cleaving of the OTS tung oil, yielded the results shown in Table F below:

TABLE F

Content of fatty acids in tung oil constituent
fatty acid blend ("TOCFAB")

| Component | % of Total |
|---|---|
| Palmitic acid | 14.93 |
| Linoleic | 11.54 |
| Oleic | 39.21 |
| Stearic acid | 13.37 |
| α-linolenic | 20.95 |
| Total | 100.00% |

Again, note the extremely unexpected differences from Table E to Table F in the fractions of identical fatty acids, apparently resulting from the process steps of the invention.

Example 2

Synthesis of Thermal Reaction Product of Isobutyl Methacrylate and Linseed Oil Constituent Fatty Acid Blend 259 g of linseed oil constituent fatty acid blend ("LOCFAB") was charged to a three neck round bottom flask, equipped with glass agitator, reflux condenser, thermometer and nitrogen purge line and heated with heating mantle to 250° F. at a rate 3 degree F. per minute. When the temperature reached 250° F., 95 g of isobutyl methacrylate was added. The mixture was heated until a temperature range 385° F. with temperature readings recorded every 2 minutes. The mixture remained at this temperature even though heating continued (indicating endothermic phase transition) and yielded a clear pill. The heat setting was kept constant. The temperature was monitored every two minutes and a plot was generated of temperature vs. time (FIG. 1).

A major endothermic event occurred at 380 degrees Fahrenheit where a temperature drop occurred and the temperature ceased to rise indicating a phase transition and the creation of the thermal reaction product. The samples shown in Tables 1 and 2 below were sent to American Polymer Standards Corporation for gel permeation chromatography to determine the molecular weight (Table 1 and Table 2).

TABLE 1

Before Thermal Reaction [A]

| Sample | Mn | Mw | Mz | Mw/Mn |
|---|---|---|---|---|
| LOCFAB | 360 | 420 | 480 | 1.17 |
| LO + IBMA | 1020 | 1160 | 1300 | 1.14 |
| LOCFAB + IBMA | 340 | 400 | 500 | 1.18 |

[A] Note:
All molecular weights are in Daltons

TABLE 2

After Thermal Reaction [A]

| Sample | Mn | Mw | Mz | Mw/Mn |
|---|---|---|---|---|
| LO + IBMA | 56500 | 95800 | 155300 | 1.7 |
| LOCFAB + IBMA | 109100 | 300400 | 648200 | 2.75 |

[A] Note:
All molecular weights are in Daltons

In this specification including Tables 1 and 2, (Mn) is the number average molecular weight, (Mw) is the average molecular weight, and (Mz) is the Z-average molecular weight.

The endothermic event at 380 degrees F. indicates that a phase transition reaction occurred. Comparison in Table 2 of the molecular weights between the LO+IBMA thermal reaction product and the LOCFAB+IBMA thermal reaction product indicates that two different polymers were formed, which were separate and unique from any of the other constituents.

The same thermal reactions as above were performed on the following.

1. LO+IBMA
2. SO+IBMA
3. TO+IBMA
4. LOCFAB+IBMA
5. SOCFAB+IBMA
6. TOCFAB+IBMA

The same endothermic phase transition occurred at 380 degrees Fahrenheit on each indicating the formation of a thermal reaction product. Differential Scanning calorimetry (DSC) was performed on each of the reaction products (See the plots of DSCs in FIGS. 2 through 7. Each reaction product exhibited a unique phase transition on the DSC as follows.

1. LO+IBMA—Phase Transition Temperature 101.66 Celsius
2. SO+IBMA—Phase Transition Temperature 132.52 Celsius
3. TO+IBMA—Phase Transition Temperature 85.98 Celsius
4. LOCFAB+IBMA—Phase Transition Temperature 71.14 Celsius
5. SOCFAB+IBMA—Phase Transition Temperature 12.37 Celsius
6. TOCFAB+IBMA—Phase Transition Temperature 106.05 Celsius The different temperatures in the events on the DSC indicate that a novel product was formed in each reaction.

Example 3

Performance Testing of Reaction Products

Cellulose based tissue paper was infused with each one of the previously mentioned thermal reaction products and the polymer was caused to cure. The infused tissue paper was shredded into uniform small pieces. Two 400 mL beakers were charged with 200 mL of water and two grams of crude oil. 0.2 Grams of linseed oil (LO)+IBMA treated tissue paper were added to one beaker and 0.2 grams of linseed constituent fatty acids blend (LOCFAB)+IBMA were added to the second beaker. The beakers were agitated with a glass stirring rod causing the oil to form a cohesive mass in conjunction with the treated tissue paper. The coagulated tissue paper oily mass was removed and a solvent extraction was performed on each of the beakers with 20 mL of trichlorotrifluoroethane in a separatory funnel. The trichlorotrifluoroethane fraction was separated and analyzed on an infrared spectrometer for absorbance. The LO+IBMA sample had a total absorbance of 1344. The LOCFAB+IBMA sample had a total absorbance of 777. The results indicate that the LOCFAB+IBMA was significantly more effective at coagulating the oil than LO+IBMA reaction product.

Example 4

Performance Testing of Reaction Products on Filters 5 inch by 2½ inch sample melt blown polypropylene filters were treated with a 10% composition of the following reaction products:

1. LO+IBMA
2. SO+IBMA
3. LOCFAB+IBMA
4. SOCFAB+IBMA

Figure 8:
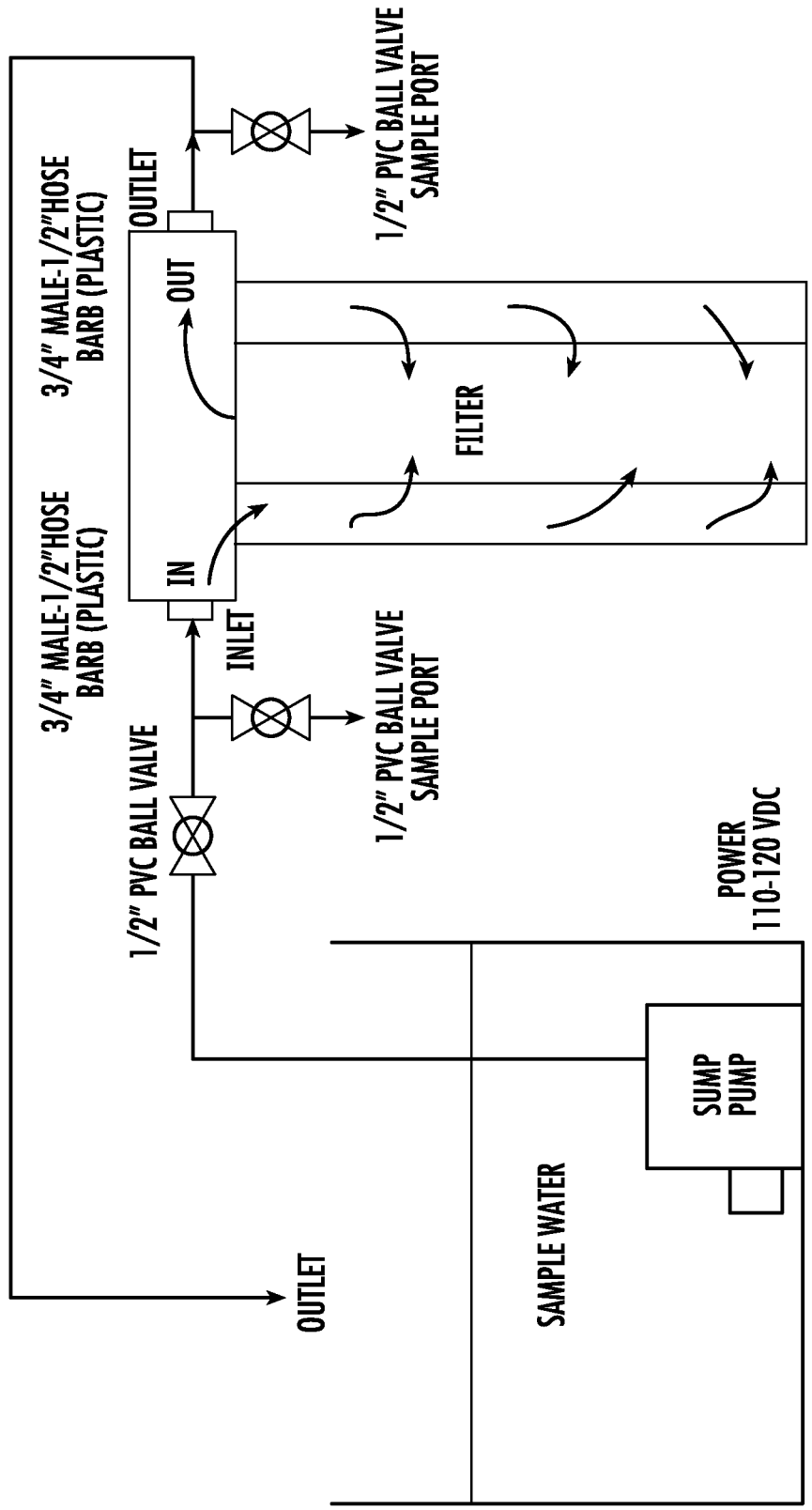
FIG. 8 is a schematic diagram depicting a testing system used to evaluate the performance of products of the invention when used as impregnants in a filtration substrate.

As illustrated in the schematic diagram of FIG. 8, the filters were engaged in recirculating apparatus with water and crude oil was injected directly into the pump inlet in increments of 20 mL until breakthrough was visible at the outlet. The filters with thermal reaction products with 1 and 2 shown in this example broke through after a total of 180 mL of crude oil. The filters with thermal reaction products 3 and 4 shown in this example did not break through and there remained a visible core of approximately ⅓ of an inch of unconsumed filter material, indicating that reaction products 3 and 4 formed a more cohesive coagulate with the oil.

Example 5

Further Performance Testing of Reaction Products on Filters

Two 5 inch by 2½ inch sample melt blown polypropylene filters were treated with a 10% composition of the following thermal reaction products:

1. LO+IBMA
2. SO+IBMA
3. LOCFAB+IBMA
4. SOCFAB+IBMA

The filters (again see FIG. 8) were engaged in recirculating apparatus with four gallon water and crude oil was injected directly into the pump inlet in increments of 20 mL until breakthrough was visible at the outlet. The filters with thermal reaction products 1 and 2 broke through after a total of 180 mL of crude oil. The filters with thermal reaction products 3 and 4 did not break through up to 390 ml of crude oil, indicating that reaction products 3 and 4 formed a more cohesive coagulate with the oil.

While the present invention has been set forth in terms of specific embodiments thereof, the instant disclosure is such that numerous variations upon the invention are now enabled to those skilled in the art, which variations yet reside within the scope of the present teaching. Accordingly, the invention is to be construed by broadly interpreting the scope and spirit of the present disclosure.

What is claimed is:

1. A method for producing a contaminant separation composition for use in removal of dispersed, solubilized, and/or emulsified oils, hydrocarbons, microbes, end toxins, triglycerides, and cholesterol from water and benign gases; comprising:
   (a) providing an initial glyceride composition comprising one or more drying oils and/or semi-drying oils;
   (b) cleaving and separating purified fatty acids from said glyceride composition, to thereby yield a blend comprised of purified saturated and mono and poly unsaturated fatty acids, said fatty acid blend being unique to said initial glyceride composition; and (c) thermally reacting said fatty acid blend from step (b) with a methacrylate or acrylate compound to yield a homogeneous thermal reaction product as said contaminant removal composition.

2. A method in accordance with claim 1, wherein said drying and/or semi-drying oils in said initial glyceride composition comprise polyunsaturated glyceride esters of fatty acids containing one or more double bonds, in which at least two of the fatty acids contain conjugated double bonds.

3. A method in accordance with claim 1, wherein said cleaving of said fatty acids is effected by saponification of said initial glyceride composition, followed by acid neutralization of the resulting soap to free the fatty acids therein.

4. A method in accordance with claim 1, wherein said cleaving of each said fatty acid is effected by hydrolyzing the ester bond of the corresponding glyceride in said initial glyceride composition, freeing the fatty acid together with glycerin, followed by said separation of the fatty acid to comprise the said fatty acid blend for said subsequent thermal reaction.

5. A method in accordance with claim 1 wherein said starting glyceride composition is selected from one or more members of the group consisting of linseed oil, safflower oil, tung oil, soybean oil, menhaden oil, hemp oil, sunflower oil, rapeseed oil, and mixtures thereof.

6. A method in accordance with claim 1, wherein said drying oils have an Iodine Number greater than 130, and said semi-drying oils have an Iodine Number in the range of 115 to 130.

7. A method in accordance with claim 1, wherein said fatty acid blend comprises alpha-linolenic acid, gamma-linolenic acid, palmitoleic acid, palmitic acid, linoleic acid, oleic acid, or stearic acid.

8. A method in accordance with claim 1, wherein said methacrylate or acrylate compound comprises isobutyl methacrylate or n-butyl methacrylate.

9. A method in accordance with claim 1, wherein the step (c) of thermally reacting said fatty acid blend with a methacrylate or acrylate compound is carried out in the presence of a solvent.

10. A method in accordance with claim 1 wherein the step (c) of thermally reacting said fatty acid blend with a methacrylate or acrylate compound is carried out in the absence of a solvent.

* * * * *